United States Patent [19]

Rose et al.

[11] Patent Number: 4,487,607

[45] Date of Patent: Dec. 11, 1984

[54] OXIDATION HAIR DYES CONTAINING 5-HALO-2,3-PYRIDINE-DIOLS AS COUPLER COMPONENTS

[75] Inventors: David Rose, Hilden; Norbert Maak, Neuss, both of Fed. Rep. of Germany

[73] Assignee: Henkel Kommanditgesellschaft auf Aktien, Düsseldorf-Holthausen, Fed. Rep. of Germany

[21] Appl. No.: 371,131

[22] Filed: Apr. 23, 1982

[30] Foreign Application Priority Data

Dec. 9, 1981 [DE] Fed. Rep. of Germany ....... 3148651

[51] Int. Cl.³ .................................................. A61K 7/13
[52] U.S. Cl. ............................................. 8/408; 8/409
[58] Field of Search ................................... 8/408, 409

[56] References Cited

U.S. PATENT DOCUMENTS 3,471,506 10/1969 Lei et al. ............................... 424/263
4,279,613 7/1981 Konrad et al. .......................... 8/410
4,288,622 9/1981 Kalopissis et al. ..................... 8/410
4,314,810 2/1982 Fourcadier et al. .................... 8/410
4,361,421 11/1982 Bugaut et al. .......................... 8/410

FOREIGN PATENT DOCUMENTS 1340270 12/1973 United Kingdom .

OTHER PUBLICATIONS

Chem. Abstracts, 97:133353s, 1982.

*Primary Examiner*—Albert T. Meyers
*Assistant Examiner*—John M. Kilcoyne
*Attorney, Agent, or Firm*—Hammond & Littell, Weissenberger & Dippert

[57] ABSTRACT

The present invention is directed to oxidation hair dyes of the developer-coupler type where the coupler component is a 5-halo-2,3-pyridine-diol and the developer component is selected from conventional developers used in hair dyeing.

11 Claims, No Drawings

OXIDATION HAIR DYES CONTAINING 5-HALO-2,3-PYRIDINE-DIOLS AS COUPLER COMPONENTS

BACKGROUND OF THE INVENTION

Oxidation dyes are formed when a developer component couples with a coupler component under oxidative conditions. These oxidative dyes are preferred in dyeing human hair since they produce intense color and usually possess satisfactory fastness.

Good oxidation hair dyes must meet the following requirements:

They must form by oxidative coupling of respective developer-coupler combinations the desired color tones of sufficient intensity. The dyes must also have good substantivity on human hair, and should be toxicologically and dermatologically safe.

Couplers which are known in oxidative dye systems include derivatives of m-phenylene diamine, phenols, naphthols, derivatives of resorcinal and pyrazolones. Well known developers such as p-phenylenediamine derivatives, diaminopyridines, 4-amino-pyrazolone and heterocyclic hydrazones are generally used in oxidation dye systems.

Oxidation dyes for hair are supplied in many cosmetic forms such as creams, emulsions, gels, or simple solutions. These are obtained in a conventional manner by mixing the coupler and developer with the usual vehicles and aids. Among these components are wetting agents and emulsifiers of the anionic and non-ionic type such as alkylbenzene sulfonates, fatty alcohol sulfates, alkyl sulfonates, fatty acid alkanolamides and the addition products of ethylene oxide and fatty alcohols; thickeners such as methyl cellulose, starch, higher fatty alcohols. Other ingredients which may also be included would be paraffin oils, fatty acids, perfumes and hair conditioners such as pantothenic acid or cholesterol.

The oxidative coupling of the oxidation dye components can occur by simple exposure to atmospheric oxygen. This is a slow process so as a rule chemical oxidizing agents are used. Hydrogen peroxide or its addition products with urea, melamine or sodium borate are commonly used.

OBJECTS OF THE INVENTION

It is an object of the present invention to provide as coupler components in oxidation dye systems 5-halo-2,3-pyridine-diols.

It is a further object of the present invention to provide a method of dyeing hair with oxidation dyes the couplers of which are 5-halo-2,3-pyridine-diols.

It is a further object of this invention to provide a hair dye of the oxidation type which contains as a coupler 5-halo-2,3-pyridine-diols of the formula

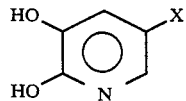

wherein X is chlorine or bromine.

These and other objects of the invention will become more apparent as the description thereof proceeds.

DESCRIPTION OF THE INVENTION

The subject of the present invention are hair dyes of the oxidation type which contain as a coupler, a 5-halo-2,3-pyridine-diol. These diols have been found to be excellent couplers for oxidation dye systems when used in combination with a number of conventional developer compounds. These 5-halo-2,3-pyridine-diols yield, with a number of developer-components, colors of particular intensity, primarily in the red to ruby range. These hair dyes are distinguished by good fastness to light and thermal stability. They are toxiologically and dermatologically harmless. The coupler components according to the invention can be used as such, but also can be used in the form of their inorganic or organic acid salts.

Practically any known developer system can be used for the couplers of the present invention. Preferred developers for use with the couplers of the present invention are aromatic and heterocyclic diamines such as 2,4,5,6-tetraaminopyrimidine, p-phenylene diamine, p-toluene diamine, 2-chloro-p-phenylene diamine, heterocyclic hydrazones and diamine pyridines.

The coupler substances according to the invention and the said developer substances are known from the literature. The production of 5-chloro-2,3-pyridine-diol is described in DE-OS 16 95 035.

The oxidation hair dyes of the invention use about equimolar amounts of couplers and developers. However a slight excess of either with respect to the other has not been found to be detrimental to the successful use of the dye system.

The hair dyes of the present invention may be used in combination with known couplers and even mixtures of developers. They may also contain directly absorbable dyes. These combinations of components may be used to obtain special color tones.

The oxidation hair dyes of the present invention can be incorporated in conventional cosmetic preparations such as creams, emulsions, gels or simple solutions. The particular composition is applied to the hair of the subject and then a conventional oxidizing agent is applied.

The concentration of coupler-developer combination in these hair dye compositions is in the range of 0.2 to 5%, by weight, preferably 1 to 3%, by weight based on the weight of the entire composition. The inclusion of the oxidation dye systems in conventional cosmetic forms such as creams, emulsions, gels or solution presents no difficulty since the couplers of the present invention are compatible with said cosmetic forms.

The oxidation hair dye compositions of the present invention, in whatsoever form, may be weakly acidic, neutral or preferably in an alkaline medium having a pH of about 8 to about 10. The application temperature should be between about 15° C. and 40°. The hair dye composition plus oxidizing agent are allowed to remain in contact with the hair for about 30 minutes. They are then rinsed from the hair with water and the hair is then washed with a mild shampoo and dried.

The following examples are provided by way of illustration and not limitation. They are not to be construed as limiting the invention thereto.

EXAMPLE I

The oxidation hair dye coupler-developer combination are combined with conventional materials to form a cream emulsion according to the following recipe:

0.01 mol of coupler
0.01 mol of developer
are blended in
10 parts by weight C$_{12}$ to C$_{18}$ fatty alcohols 10 parts by weight $C_{12}$ to $C_{18}$ fatty alcohol sulfate (sodium salt)
75 parts by weight water The pH of the emulsion was adjusted with ammonia to 9.5. The total weight of the composition was made up to 100 parts by weight with the addition of water.

The oxidative coupling of the couplers of the invention and selected developers is effected using a 3% solution of hydrogen peroxide as the oxidizing agent.

Tresses of 90% gray human hair were treated with dye compositions each of which included a coupler of the present invention and a selected developer. After addition of the oxidizing agent, the cream emulsions containing the various coupler-developer compositions were applied to individual tresses and allowed to act for thirty minutes. After thirty minutes the hair was washed in a mild, conventional shampoo and dried. The resulting colors were as follows:

TABLE I

Oxidation Dye Combination (Oxidizing Agent 3% $H_2O_2$ aqueous solution)

| | Developer | Coupler | Color of Dyed Hair |
|---|---|---|---|
| 1. | p-phenylene-diamine | 5-chloro-2,3-pyridine-diol | violet-brown |
| 2. | N,N—Dimethyl-p-phenylenediamine | " | dark ruby |
| 3. | N—butyl-N—sulfobutyl-p-phenylene-diamine | " | gray-brown |
| 4. | 2-Chloro-p-phenylenediamine | " | red-brown |
| 5. | N—ethyl-N—Beta-hydroxyethyl-p-phenylenediamine | " | dark ruby |
| 6. | 2-Methylamino-4,5,6-triamino-pyrimidine | " | brown-orange |
| 7. | 2,5-Diaminopyridine | " | red-brown |
| 8. | N—2-hydroxypropyl-p-phenylene-diamine | " | red-brown |
| 9. | N—Methyl-p-phenylenediamine | " | violet-brown |
| 10. | 2,4,5,6-Tetraaminopyrimidine | " | gray-brown |
| 11. | p-Toluylenediamine | " | red-brown |
| 12. | N—(p-Aminophenyl)-N',N'—bis-(Beta-hydroxyethyl)-1,3-diaminopropane | " | violet-brown |
| 13. | p-Toluylenediamine | 5-Bromo-2,3-pyridine-diol | red-brown |
| 14. | 2,4,5,6-Tetraaminopyrimidine | " | gray-brown |

The preceding specific embodiments are illustrative of the practice of the present invention. It is to be understood, however, that variations which may be obvious to those skilled in the art or suggested herein, may be employed without departing from the spirit of the invention or the scope of the appended claims.

We claim:

1. An oxidation dye composition for dyeing human hair comprising in substantially equal molar amounts:
   (a) one or more components selected from the group consisting of 5-chloro-2,3-pyridine-diol, 5-bromo-2,3-pyridine-diol, and inorganic or organic acid salts thereof; and
   (b) a developer component.

2. The composition of claim 1, wherein the developer component (b) comprises one or more aromatic or heterocyclic diamines.

3. The composition of claim 2, wherein the developer component (b) comprises one or more compounds selected from the group consisting of 2,4,5,6-tetraaminopyrimidine, p-phenylene diamine, p-toluene diamine, 2-chloro-p-phenylene diamine, heterocyclic hydrazones, and diamine pyridines.

4. The composition of claim 1, wherein the composition comprises from about 0.2 to 5 percent by weight of developer-coupler combination.

5. The composition of claim 4, wherein the composition comprises from about 1 to 3 percent by weight of the developer-coupler combination.

6. A method for the dyeing of human hair comprising applying to said hair, at temperatures ranging from about 15° to 40° C. for a time sufficient to effect dyeing through oxidation, an effective amount of the developer-coupler composition according to claim 1.

7. The method of claim 6, wherein the oxidation is effected by the action of an oxidation agent.

8. An oxidation dye composition for dyeing human hair comprising in substantially equal molar amounts:
   (a) 5-chloro-2,3-pyridine-diol; and
   (b) a developer component comprising one or more compounds selected from the group consisting of 2,4,5,6-tetraaminopyrimidine, p-phenylene diamine, p-toluene diamine, 2-chloro-p-phenylene diamine, heterocyclic hydrazones, and diamine pyridines.

9. An oxidation dye composition for dyeing human hair comprising in substantially equal molar amounts:
   (a) 5-bromo-2,3-pyridine-diol; and
   (b) a developer component comprising one or more compounds selected from the group consisting of 2,4,5,6-tetraaminopyrimidine, p-phenylene diamine, p-toluene diamine, 2-chloro-p-phenylene diamine, heterocyclic hydrazones, and diamine pyridines.

10. An oxidation dye composition for dyeing human hair consisting essentially of:
    (a) 0.01 mol of a coupler selected from the group consisting of 5-chloro-2,3 pyridine-diol and 5-bromo-2,3-pyridine-diol;
    (b) 0.01 mol of a developer comprising one or more compounds selected from the group consisting of 2,4,5,6-tetraaminopyrimidine, p-phenylene diamine, p-toluene diamine, 2-chloro-p-phenylene diamine, heterocyclic hydrazones, and diamine pyridines;

(c) 10 parts by weight of at least one $C_{12}$- to $C_{18}$-fatty alcohol;
(d) 10 parts by weight of at least one $C_{12}$- to $C_{18}$-fatty alcohol sodium sulfate; and
(e) 75 parts by weight water.

11. A method for the dyeing of human hair comprising applying to said hair, at a temperature ranging from about 15° to 40° C. for a time sufficient to effect dyeing through oxidation, an effective amount of the composition of claim 10.

* * * * *

UNITED STATES PATENT AND TRADEMARK OFFICE
CERTIFICATE OF CORRECTION

PATENT NO. : 4,487,607

DATED : December 11, 1984

INVENTOR(S) : DAVID ROSE et al.

It is certified that error appears in the above-identified patent and that said Letters Patent is hereby corrected as shown below:

Column 1, line 67, "are" should read -- is --.

Column 2, line 52, "40°" should read -- 40°C --.

Column 2, line 55, "water" should read -- water, --.

Column 2, line 63, "tion" should read -- tions --.

Column 3, line 55, "components" should read -- coupler components --.

Column 4, line 61, "5-chloro-2,3 pyridine-diol" should read

-- 5-chloro-2,3-pyridine-diol --.

Signed and Sealed this

Third Day of September 1985

[SEAL]

Attest:

DONALD J. QUIGG

Attesting Officer    Acting Commissioner of Patents and Trademarks - Designate